(12) United States Patent
Weingärtner et al.

(10) Patent No.: US 12,352,835 B2
(45) Date of Patent: Jul. 8, 2025

(54) METHOD AND APPARATUS FOR MAGNETIC RESONANCE IMAGING

(71) Applicant: TECHNISCHE UNIVERSITEIT DELFT, Delft (NL)

(72) Inventors: Sebastian Daniel Weingärtner, Delft (NL); Paulina Šiurytė, Delft (NL); João Luis Silva Canaveira Tourais, Delft (NL)

(73) Assignee: TECHNISCHE UNIVERSITEIT DELFT, Delft (NL)

( * ) Notice: Subject to any disclaimer, the term of this patent is extended or adjusted under 35 U.S.C. 154(b) by 159 days.

(21) Appl. No.: 18/250,370

(22) PCT Filed: Oct. 28, 2021

(86) PCT No.: PCT/NL2021/050657
§ 371 (c)(1),
(2) Date: Apr. 25, 2023

(87) PCT Pub. No.: WO2022/093023
PCT Pub. Date: May 5, 2022

(65) Prior Publication Data
US 2024/0019513 A1    Jan. 18, 2024

(30) Foreign Application Priority Data
Oct. 28, 2020   (NL) ..................... 2026785

(51) Int. Cl.
*G01V 3/00* (2006.01)
*A61B 5/055* (2006.01)
(Continued)

(52) U.S. Cl.
CPC .......... *G01R 33/3854* (2013.01); *A61B 5/055* (2013.01); *G01R 33/543* (2013.01); *G01R 33/58* (2013.01); *G06N 3/096* (2023.01)

(58) Field of Classification Search
CPC .. G01R 33/485; G01R 33/4828; G06T 11/008
(Continued)

(56) References Cited

U.S. PATENT DOCUMENTS 5,427,102 A   6/1995   Shimode et al.
5,481,192 A   1/1996   Mehlkopf et al.
(Continued)

FOREIGN PATENT DOCUMENTS

DE   10 2013 218 309 A1   3/2015
EP      3 575 811 A1    12/2019
(Continued)

OTHER PUBLICATIONS

Li, M., Rudd, B., Lim, T.C. and Lee, J.H., 2011. In situ active control of noise in a 4 T MRI scanner. Journal of Magnetic Resonance Imaging, 34(3), pp. 662-669.
(Continued)

*Primary Examiner* — Walter L Lindsay, Jr.
*Assistant Examiner* — Frederick Wenderoth
(74) *Attorney, Agent, or Firm* — N.V. Nederlandsch Octrooibureau

(57) ABSTRACT

Method for magnetic resonance imaging, MRI, comprising obtaining an image acquisition sequence comprising RF pulses and magnetic field gradients configured to encode spatial information in a part of an object; obtaining an acoustic noise cancelling signal corresponding to the obtained image acquisition sequence at a first position; generating the image acquisition sequence; wherein the magnetic fields gradients are generated by gradient coils configured for three orthogonal directions respectively; and converting, by an acoustic transducer, simultaneously with the image acquisition sequence, the predetermined noise cancelling signal to an acoustic noise cancelling signal at the first position. The noise cancelling signal is obtained based
(Continued)

on an acoustic transfer function and the magnetic field gradients of the image acquisition sequence, wherein the acoustic transfer function is obtained by training a neural network on a plurality of generic image acquisition sequences followed by transfer learning with calibration image acquisition sequences obtained during a calibration state before the generating of the image acquisition sequence.

20 Claims, 2 Drawing Sheets

(51) Int. Cl.
*G01R 33/385* (2006.01)
*G01R 33/54* (2006.01)
*G01R 33/58* (2006.01)
*G06N 3/096* (2023.01)

(58) Field of Classification Search
USPC .......................................................... 324/309
See application file for complete search history.

(56) References Cited

U.S. PATENT DOCUMENTS

| | | | |
|---|---|---|---|
| 6,463,316 B1 * | 10/2002 | Brungart | G10K 11/17861 381/72 |
| 6,954,666 B2 | 10/2005 | Bechtold et al. | |
| 9,438,981 B2 | 9/2016 | Brown et al. | |
| 2003/0212328 A1 | 11/2003 | Bechtold et al. | |
| 2014/0300358 A1 | 10/2014 | Rapoport | |
| 2015/0004233 A1 | 2/2015 | Grodzki | |
| 2015/0260817 A1 | 9/2015 | Grodzki | |
| 2017/0029069 A1 | 2/2017 | Deurr et al. | |

FOREIGN PATENT DOCUMENTS

| | | | | |
|---|---|---|---|---|
| EP | 3 633 601 A1 | 4/2020 | | |
| GB | 2413917 A * | 11/2005 | ......... | G01R 33/3854 |
| WO | WO-2009074918 A1 * | 6/2009 | ......... | G01R 33/3854 |

OTHER PUBLICATIONS

Rudd, B.W., Lim, T.C., Li, M. and Lee, J.H., 2012. In situ active noise cancellation applied to magnetic resonance imaging.

Goldman, A.M., Gossman, W.E. and Friedlander, P.C., 1989. Reduction of sound levels with antinoise in MR imaging. Radiology, 173(2), pp. 549-550.

McJury, M., Stewart, R.W., Crawford, D. and Toma, E., 1997. The use of active noise control (ANC) to reduce acoustic noise generated during MRI scanning: some initial results. Magnetic resonance imaging, 15(3), pp. 319-322.

Mechefske, C.K., Geris, R., Gati, U.S. and Rutt, B.K., 2001. Acoustic noise reduction in a 4 T MRI scanner. Magnetic Resonance Materials in Physics, Biology and Medicine, 13, pp. 172-176.

Chambers, J., Akeroyd, M.A., Summerfield, A.Q. and Palmer, A.R., 2001. Active control of the volume acquisition noise in functional magnetic resonance imaging: method and psychoacoustical evaluation. The Journal of the Acoustical Society of America, 110(6), pp. 3041-3054.

Hamaguchi, T., Miyati, T., Ohno, N., Hirano, M., Hayashi, N., Gabata, T., Matsui, O., Matsushita, T., Yamamoto, T., Fujiwara, Y. and Kimura, H., 2011. Acoustic noise transfer function in clinical MRI: a multicenter analysis. Academic radiology, 18(1), pp. 101-106.

Hall, D.A., Chambers, J., Akeroyd, M.A., Foster, J.R., Coxon, R. and Palmer, A.R., 2009. Acoustic, psychophysical, and neuroimaging measurements of the effectiveness of active cancellation during auditory functional magnetic resonance imaging. The Journal of the Acoustical Society of America, 125(1), pp. 347-359.

NessAiver, M.S., Stone, M., Parthasarathy, V., Kahana, Y. and Paritsky, A., 2006. Recording high quality speech during tagged cine—MRI studies using a fiber optic microphone. Journal of Magnetic Resonance Imaging: An Official Journal of the International Society for Magnetic Resonance in Medicine, 23(1), pp. 92-97.

Lee, N., Park, Y. and Lee, G.W., 2017. Frequency-domain active noise control for magnetic resonance imaging acoustic noise. Applied Acoustics, 118, pp. 30-38.

Inouye, J.M., Blemker, S.S. and Inouye, D.I., 2014. Towards undistorted and noise-free speech in an MRI scanner: correlation subtraction followed by spectral noise gating. The Journal of the Acoustical Society of America, 135(3), pp. 1019-1022.

Vemuri, S.H.K., Ganguly, A. and Panahi, I., Oct. 2014. Real-time active noise control of multi-tones and MRI acoustic noise in fMRI bore with signal decomposition and parallel hybrid RLS-NLMS adaptive algorithms. In 2014 IEEE Dallas Circuits and Systems Conference (DCAS) (pp. 1-4). IEEE.

Carlos Vicente Rizzo Sierra, "Magnetic resonance imaging (MRI) accoustic noise: Estimation, characterization and reduction. s.n." 2008.

Kannan, "An Efficient Feedback Active Noise Control Algorithm Based on Reduced-Order Linear Predictive Modeling of fMRI Acoustic Noise", IEEE Transactions on Biomedical Engineering, vol. 58, No. 12, Dec. 2011, p. 3303-3309.

Lecun et al., "Gradient-Based Learning Applied to Document Recognition", Proceedings of the IEEE, vol. 86, No. 11, Nov. 1998, p. 2278-2324.

Kingma et al., "ADAM: A Method for Stochastic Optimization", 2015.

Hochreiter et al., "Long Short-Term Memory", Neural Computation 9, 1735-1780 (1997) ° C. 1997 Massachusetts Institute of Technology.

* cited by examiner

METHOD AND APPARATUS FOR MAGNETIC RESONANCE IMAGING

FIELD OF THE INVENTION

The invention relates to a method and apparatus for magnetic resonance imaging.

BACKGROUND OF THE INVENTION

Magnetic resonance imaging, MRI, is one of the leading medical imaging modalities with millions of scans performed each year. While MRIO is not directly harmful to the body, long scan time and loud acoustic noise are major sources of patient discomfort and, in some cases, sustained exposure to loud noise can even result in permanent hearing damage. A known method to reduce acoustic noise is to use active noise cancelling. A drawback of the known method is the use of real-time feedback algorithm that introduces a time-lag to reach a maximum cancelling of the MRI sound.

Another known method for noise cancelling in MRI is known from US patent application no 2017029069. That document discloses a method comprising determining a target frequency of an MRI acoustic noise signal generated in an MRI apparatus, generating a control signal for the determined target frequency and outputting the control signal wherein the target signal is the frequency of the MRI acoustic noise signal to be controlled and the control signal is a signal in which at least one of an amplitude and phase of the MRI acoustic noise signal is changed.

U.S. Pat. No. 5,481,192 discloses a magnetic resonance apparatus with noise cancellation. The device is designed to generate a compensating sound signal which is, in at least one region which is referred to as a region of silence, in phase opposition with a sound signal generated by the gradient coils of the magnetic resonance apparatus.

DE 10 2013 218 309 A1 also discloses a device for active sound suppression of a magnetic resonance apparatus.

SUMMARY OF THE INVENTION

It is an object of the invention to provide a method and apparatus for MRI with a reduced acoustic noise output.

According to a first aspect of the invention this object is achieved by a method for magnetic resonance imaging, MRI, comprising obtaining an image acquisition sequence comprising RF pulses and magnetic field gradients configured to encode spatial information in a part of an object in an MRI apparatus; obtaining a noise cancelling signal corresponding to the obtained image acquisition sequence at a first position inside the MRI apparatus; generating the image acquisition sequence, wherein the magnetic fields gradients are generated by three gradient coils provided in the MRI apparatus configured for three orthogonal directions respectively, and converting, by an acoustic transducer, simultaneously with the image acquisition sequence, the predetermined noise cancelling signal to an acoustic noise cancelling signal at the first position. In an embodiment, the noise cancelling signal is obtained based on an acoustic transfer function and the magnetic field gradients of the image acquisition sequence. In an embodiment, the noise cancelling signal is obtained based on an acoustic transfer function and the magnetic field gradients of the image acquisition sequence, wherein the acoustic transfer function is obtained by training a neural network on a plurality of generic image acquisition sequences followed by transfer learning with calibration image acquisition sequences obtained during a calibration state before the generating of the image acquisition sequence.

Training the neural network can comprise providing (generic) image acquisition sequences and the corresponding acoustic noise to the network, so that the network learns the non-linear or linear transfer function from image acquisition sequence to acoustic noise. Transfer learning can comprise retraining the already trained neural network (that was trained using e.g. image acquisition sequences from a generic MRI apparatus or a number of MRI apparatus) using calibration image acquisition sequences that are obtained just prior to generating the image acquisition sequence on the MRI apparatus that is currently being used. In that way, specific differences in e.g. the MRI apparatus, it's surroundings, and/or the positioning and unique shape of the patient can be accounted for.

In this way an optimum noise cancelling signal can be determined in advance that corresponds to the noise generated by the gradient coils due to the varying currents directed through the gradient coils to generate the magnetic gradient fields of the image acquisition sequence. Because the noise cancelling signal is determined in advance adjustments can be made to optimally reduce the noise. In this disclosure noise is always intended acoustic noise.

An insight of the invention is that as a first approach the acoustic noise generated by the gradient coils scales linearly with the derivatives of the currents through the gradient coils and a linear model can be applied and as a second approach a non-linear model of the acoustic noise as function of the derivatives of the currents through the gradient coils can be applied. Known machine learning methods can be applied for arbitrary function approximation, for example convolutional neural network, CNN, as known from CNN: LeCun, Yann; Leon Bottou; Yoshua Bengio; Patrick Haffner (1998). "Gradient-based learning applied to document recognition" (PDF), Proceedings of the IEEE. 86 (11): 2278-2324, doi: 10.1109/5.726791. Retrieved Nov. 16, 2013, and temporal recurrent neural networks, for example long short-term memory, LSTM, as known from LSTM: Sepp Hochreiter; Jurgen Schmidhuber (1997). "Long short-term memory". Neural Computation. 9 (8): 1735-1780. oi:10.1162/ neco.1997.9.8.1735. PMID 9377276. S2CID 1915014.

According to a second aspect of the invention this object is achieved by an apparatus for magnetic resonance imaging of an object comprising: RF coils for generating RF pulses; gradient coils for generating gradient magnetic fields in three orthogonal directions respectively; an acoustic transducer; and a controller arranged to obtain an image acquisition sequence comprising the RF pulses and the gradient magnetic fields configured to encode spatial information in a part of the object; obtain a noise cancelling signal corresponding to the obtained image acquisition sequence at a first position;
generate the image acquisition sequence; and
control the acoustic transducer to convert the predetermined noise cancelling signal to an acoustic noise cancelling signal at the first position. In an embodiment, the noise cancelling signal is obtained based on an acoustic transfer function and the magnetic field gradients of the image acquisition sequence. In an embodiment, the noise cancelling signal is obtained based on an acoustic transfer function and the magnetic field gradients of the image acquisition sequence, wherein the acoustic transfer function is obtained by training a neural network on a plurality of generic image acquisition sequences followed by transfer learning with calibration image acquisition sequences obtained during a calibration state before the generating of the image acquisition sequence. Further advantageous embodiments are specified in the dependent claims.

The person skilled in the art will understand that the features described above may be combined in any way deemed useful. Moreover, modifications and variations described in respect of the system may likewise be applied to the method and to the computer program product, and modifications and variations described in respect of the method may likewise be applied to the system and to the computer program product.

BRIEF DESCRIPTION OF DRAWINGS

These and other aspects of this disclosure are apparent from and will be elucidated, by way of non-limitative example, with reference to the embodiments described hereinafter and the accompanying drawing. The drawings are diagrammatic and may not be drawn to scale.

In the drawing.

DETAILED DESCRIPTION OF EMBODIMENTS

Figure 1:
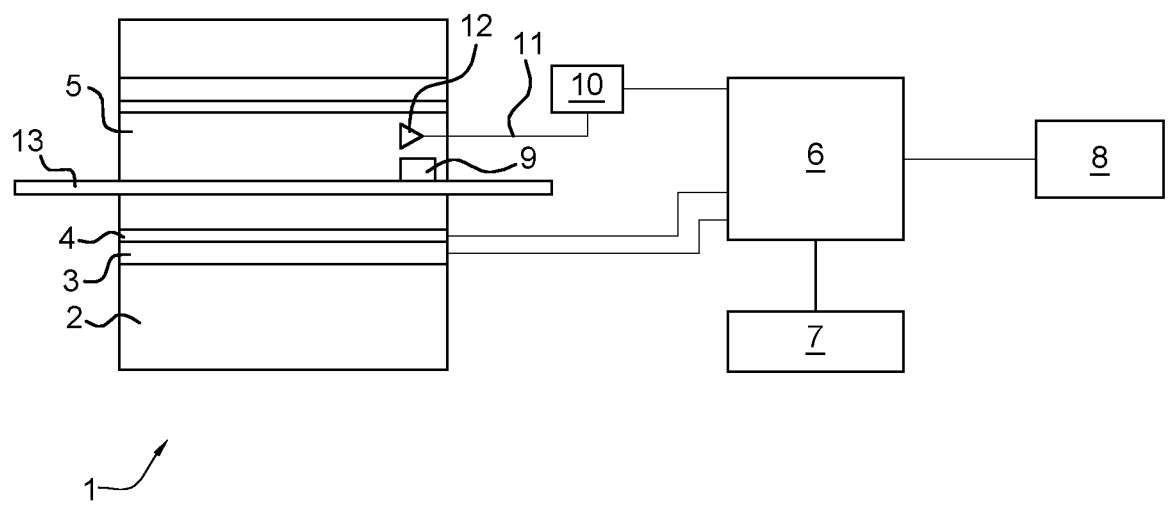
FIG. 1 shows diagrammatically a magnetic resonance imaging, MRI, apparatus according to an embodiment of this disclosure.

In the following description, a number of example embodiments will be described in more detail. However, the description of these embodiments is not intended to limit the scope of protection. However, it is noted that in view of the present disclosure, the techniques described in respect thereto may be applied in a similar way using alternative or modified mathematical models and techniques. In the drawing the same reference signs refer to like objects.

FIG. 1 shows diagrammatically a magnetic resonance imaging, MRI, apparatus 1 according to an embodiment of this disclosure. The MRI apparatus 1 is provided with a basic magnet 2, gradient coils 3 and an RF coil 4, a patient reception region 5 and a moveable patient table 13. The basis field magnet 2, the gradient coils 3 and the RF coil 4 surround the patient reception region 5. A patient on the patient table 13 can be slid into the MRI apparatus 1. The basis magnet 2 is configured to generate a constant magnet field. The basis magnet is a superconducting magnet for generating a magnetic field strength of for example 1.5 T. The gradient coils 3 are used to generate magnetic field gradients in three orthogonal directions. The magnetic field gradients are used to encode spatial information for imaging in a part of the patient on the patient table 13. The RF coils 4 are used to generate RF pulses.

The MRI apparatus 1 is further provided with a microphone 9 and an acoustic transducer 10. The microphone 9 can be, for example, an optical fiber microphone (Phonoptics, Courcouronnes, France) The microphone 9 is located at a first location in the patient reception region 5 and can be used to receive an acoustic noise signal from the gradient coils. The acoustic transducer 10 may comprise, for example, a speaker positioned outside a room where the MRI apparatus 1 is located, the speaker is connected via a tube 11 of which one opening is connected to the acoustic transducer and the other opening to a funnel 12 such that an acoustic noise cancelling signal can be transferred to the first location in the patient reception region 5. Other well-known MRI compatible acoustic transducers can also be applied, for example "MM stereo" of Sound imaging, San Diego, USA.

Furthermore, the MRI apparatus 1 comprises a controller 6, a database 7, a display and a user interface 8. The controller 6 is connected to the database 7, the display and user input 8, the gradient coils 3, the RF coil 4, the microphone 9 and the transducer 10. The database 7 can comprises information such image acquisition sequences, imaging protocols and noise-cancelling signals corresponding to the image acquisition sequences.

A general functionality of an MRI apparatus is well known to a person skilled in the art and a comprehensive description of the functionality is omitted.

In operation, when a patient is on the patient and is partly inside the patient reception region, an operator can select an imagine acquisition sequence from the database 7. The controller 6 generates the selected image acquisition sequences to obtain spatial information of the body of the patient. The generating of the image acquisition sequence comprises generating magnetic field gradients and RF pulses and acquiring RF signals comprising the encoded spatial information in accordance with the generated RF pulses and magnetic field gradients.

The controller 6 controls the currents through the respective gradient coils 3 corresponding with the selected image acquisition sequence for generating the three magnetic field gradients in the three orthogonal directions respectively. Besides these magnetic field gradients the gradient coils 3 are generating the acoustic noise due to the mechanical forces induced by the varying currents through the gradient coils.

This acoustic noise can have a loudness of, for example, in the range between to 130 dB and can be annoying or even damaging to a patient's hearing.

Conventionally, the patient in the patient reception region in the MRI apparatus is provided with ear plugs or headphones to avoid damage to the hearing. Also noise-cancelling head phones are suggested to reduce the acoustic noise.

According to this disclosure a method is provided wherein the acoustic noise-cancelling signal is generated at a position inside the patient reception region to reduce or eliminate the acoustic noise generated by the gradient coils 3.

Figure 2:
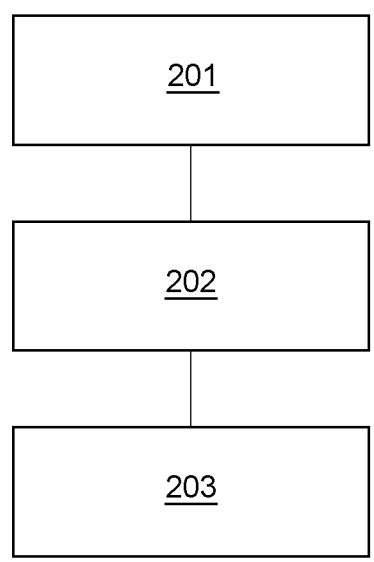
FIG. 2 shows a flow diagram of a method for noise cancelling according to an embodiment of this disclosure.

FIG. 2 shows a flow diagram of a method for acoustic noise cancelling according to this disclosure. In a step 201, the controller 6 obtains an image acquisition sequence comprising RF pulses and magnetic field gradients configured to encode spatial information in a body of the patient in the MRI apparatus. The image acquisition sequence can be selected by an operator via the display and user input 8. In an embodiment the image acquisition sequence can be echo planar imaging, EPI, sequence. Also other well knows image acquisition sequences can be used such as gradient echo, GRE, or balanced steady-state free precession, bSSFP.

In order to obtain an image acquisition sequence the operator can select the EPI sequence via the display and user interface. After the image acquisition sequence is selected, in a next step 202, the controller 6 obtains a predetermined noise cancelling signal corresponding to the selected image acquisition sequence from the database 7.

In a next step 203 the controller generates the RF pulses through the RF coils 4, the currents through the gradient coils 3 to obtain the magnetic field gradients and controls the acoustic transducer 10 to convert the noise cancelling signal in an acoustic noise cancelling signal. The acoustic noise cancelling signal is transferred via the tube 11 to the funnel 12 at the first location inside the patient reception region 5 in the MRI apparatus 1.

At the first position at which the patient's head can be located, the acoustic noise cancelling signal is substantially in anti-phase with the generated noise of the gradient coils 3 and the resulting acoustic noise is reduced, which is more convenient to the patient.

Furthermore, in correspondence with the generated RF pulses and the magnetic field gradients of the selected image acquisition sequence the controller 6 is arranged to receive the RF signals via the RF reception coils and process the RF signals comprising the encoded spatial information and stores the received signals in the database 7 for image reconstruction.

In an embodiment the controller 6 determines the noise cancelling signals of a set of image acquisition sequences in advance of the image acquisition process and stores the noise cancelling signal in the database 7. So, the database 7 comprises image acquisition sequences and corresponding noise cancelling signals.

In an embodiment according to this disclosure the noise cancelling signal corresponding to an imaging sequence can be obtained by an acoustic transfer function of the gradient coil currents corresponding to the image acquisition sequence.

The acoustic transfer function can be obtained in a calibration state, before the image acquisition process is initiated.

Figure 3:
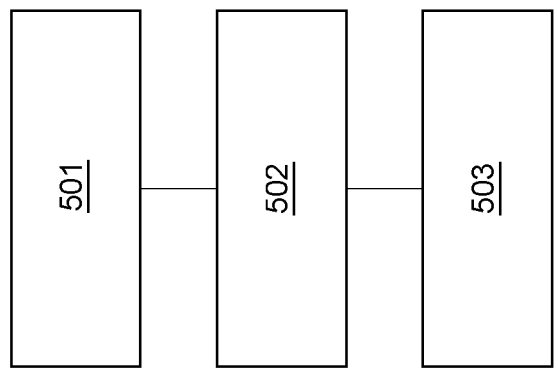
FIG. 3 shows a flow diagram for obtaining the acoustic transfer function according to an embodiment of this disclosure.

FIG. 3 shows a flow diagram of a method for obtaining the acoustic transfer function according to an embodiment of this disclosure. In this embodiment the output acoustic noise is expected to scale linearly with the input—gradient coils derivative of the gradient coil input $$\frac{\delta I(t)}{\delta t}$$

measured in gradient strength units mT/m/s.

In the frequency domain the acoustic transfer functions can be then written as $$P(f) = (Gf) \cdot H(f) \tag{1}$$

Wherein H (f) is a complex-valued, time-invariant system transfer function.

In a well-known MRI setup, the three gradient coils will be used to encode spatial information. The calibration is performed by the controller thereto the controller 6 generates in a step 301 calibration currents through the respective gradient coils 3 for generation of calibration magnetic field gradients and acquires in a further step 302, by the microphone 9 positioned at the first position, respectively a first, a second and a third signal of an acoustic response caused by the calibrations currents through the gradient coils 3. In an embodiment the controller 6 can filter the respective first, second and third response signal by a pass-band filter with a pass-band between 100 Hz and 6 kHz.

In a further step 303 the controller 6 further transforms the first, the second and the third signals to the frequency domain, for example, by using a discrete Fourier transform, DFT, and determines respectively time derivatives of the calibration currents through the gradient coils 3 and transforms the time derivatives to the frequency domain by DFT.

In a next step 304 the controller obtains the acoustic transfer function by using formula $$H_{x,y,z} = \frac{P_{x,y,z}}{G_{x,y,z}} \tag{2}$$

wherein $H_{x,y,z}$ represent respectively acoustic transfer functions corresponding to the first, the second and the third gradient coil, $G_{x,y,z}$ represent respectively the time DFT transformed time derivatives of the currents through the gradient coils to obtain the magnetic field gradients and $P_{x,y,z}$ represent the transformed first, second and third signals. The magnetic field gradient can have a value of 32 mT/m, preferably a maximum magnetic field gradient that can be obtained by the MRI apparatus. In an embodiment the accuracy of the transfer function can be improved by averaging the transfer function over for example 20 magnetic field gradients. The noise signal P can now predicted by $$P = G_x H_x + G_y H_y + G_z H_z \tag{3}$$

In an embodiment a phase adjustment is applied to the transfer function to adjust the phase of the noise cancelling signal so that the acoustic noise canceling signal is 180 degrees out of phase with the acoustic noise at the first position.

Figure 4:
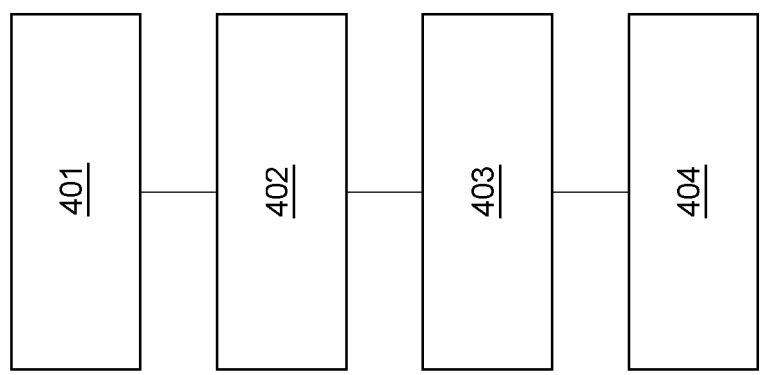
FIG. 4 shows a flow diagram for obtaining a phase adjustment of the acoustic transfer function.

$e^{-2\pi i f t p h}$ FIG. 4 shows a flow diagram of a method for obtaining a phase adjustment of the acoustic transfer function. In a step 401 controller 6 generates magnetic field gradients for two of the three orthogonal axis; acquires in a step 402, by the microphone 9 at the first position, combined signals of the acoustic response of the combined magnetic field gradients; determines 403 a predictive signal based on the transfer function and the magnetic gradients and minimizes in step 404 a difference between the acquired combined signal and the predictive signal by iterating the predictive signal over a range of values $t_{ph}$, wherein $t_{ph}$ is defined for the combinations for two of the three gradient pulses, wherein the phase correction for each transfer function $T_{rel}$=and the transfer function is $$e^{-2\pi i f t p h} H_{x/y/z} = H'_{x/y/z} \cdot T_{rel} \tag{4}$$

When the transfer function is determined and stored in the database 7 the controller 6 can determine noise cancelling signals $P_{pred}$ corresponding to the set of image acquisition sequences and protocols, for example, gradient echo, GRE, sequences, bSSFP sequences and echo planar imaging, EPI, sequences using formulas (2) and (3).

In a next step, the controller 6 obtains a noise cancelling signal corresponding to the set of image acquisition signals and stores the noise cancelling signals in the database 7.

Figure 5:
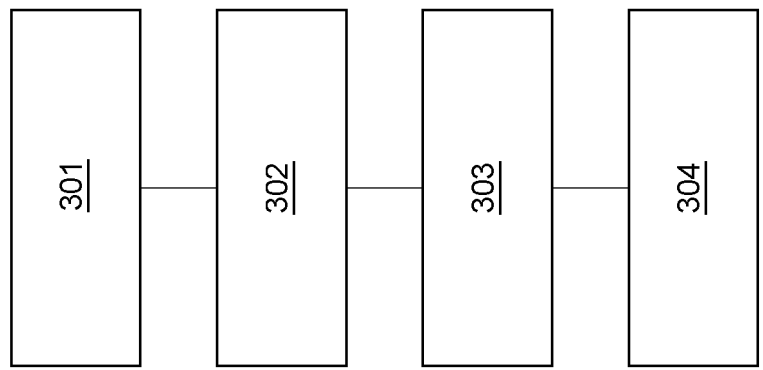
FIG. 5 shows a flow diagram to obtain an optimum noise cancelling signal of an image acquisition sequence according to an embodiment of this disclosure.

FIG. 5 shows a flow diagram of a method to obtain an optimum noise cancelling signal of an image acquisition sequence according to an embodiment of this disclosure. In step 501 the controller determines a predicted signal $P_{pred}$ by applying formulas (2), (3) and the expected currents to generate the magnetic field gradients of a first image acquisition sequence of the set. In a next step 502 the controller 6 determines a minimum $$\text{Min} = P_{meas} - P_{pred}$$

by iterating over a range tabs values in small increments, wherein $P_{pred}$ (t) is defined as P' (t-$t_{abs}$) for consecutive $t_{abs}$.

A possible signal power reduction and acoustic noise reduction of the optimum noise-cancelling signal can be estimated by respectively $$1 - \frac{|p_{meas}^2(t)|}{|p_{pred}^2(t)|} \quad (5)$$

and $$10 lg(|p_{meas}^2(t)| - 10 lg(|p_{pred}^2(t)|) \quad (6)$$

The controller 6 in a step 503 stores the optimum noise-cancelling corresponding to the first image acquisition sequence in the database 7.

In an embodiment the controller 6 can determine optimum noise cancelling signals for the set of image acquisition sequences and repeats the foregoing steps for each image acquisition sequence of the set. In this way the date base 7 can be filled with noise cancelling signals corresponding to the image acquisition sequences in the database.

In a further embodiment of this disclosure non-linear modelling of the acoustic noise as function of the derivatives of the currents through the gradient coils is applied. When a non-linear scan system representing the MRI apparatus S is characterized by calibration image acquisition sequence $P_{x,y,z}$ Equation (3) can be rewritten as $$P = fs(G_x, G_y, G_z) \quad (7)$$

Wherein $fs$ is a non-linear function. The calibration image acquisition sequences can be similar to those used for the linear model as described herein before.

According to an embodiment of this disclosure the output acoustic noise is expected to scale in accordance with a non-linear model with the input—gradient coils derivative of the gradient coil input $$\frac{\delta I(t)}{\delta t}$$

measured in gradient strength units mT/m/s.

In an embodiment of this disclosure a convolutional neural network, CNN, is trained on a plurality of imaging acquisition sequences and the controller determines a predicted signal $P_{pred}$ by applying formulas (7) and the expected currents to generate the magnetic field gradients of a plurality of different image acquisition sequences. This yields a fully trained network for determining an approximation $fs$. An example for a neural network model comprises three dense layers, an input, a hidden layer and an output layer, the nodes of the layers are fully connected, and a rectified linear activation function, ReLU. The activation function transforms a summed weighted input from a node into activation of the node or output from that node. Using an Adam optimization algorithm this neural network model will converge in about 50 epochs.

The Adam optimization algorithm is known from Diederik P. Kingma and Jimmy B A, Adam: A Method for Stochastic Optimization, 3rd International Conference on Learning Representations, ICLR 2015, San Diego, CA, USA, May 7-9, 2015, Conference Track Proceedings, CPAPER, DBLP:journals/corr/KingbaB14.

A second non-linear scan system is characterized by calibration sequences $P'_{x,y,z}$. A transfer function $fs'$ can be determined using transfer learning with the calibration image acquisition sequences $P_{x,y, and\ z}$ of the MRI apparatus.

The retrained network is using a large training set of calibration image acquisition sequences of a generic or multiple MRI apparatus, while being adapted to the current imaging acquisition sequence. The anti-noise signal is then generated from the retrained network using equation (7).

In a further embodiment according to this disclosure temporal recurrent neural networks, for example long short-term memory, LSTMs are used to train jointly on the gradients $G_x$, $G_y$, $G_z$ and the sound profile of the calibration imaging sequences. In this way a single network can be trained for a plurality of apparatus, while the calibration imaging sequences are not changed between the plurality of apparatus. This network in effect learns a function g (P, $G_x$, $G_y$, and $G_z$).

$$fs(G_x, G_y, G_z) = g(P_{x,y,z}, G_x, G_y, G_z)$$

Wherein $P_{x,y,z}$ represents the calibration image acquisition sequence of the apparatus. The anti-noise signal is then generation using equation (7).

Each of the foregoing elements of the apparatus according to the present disclosure may be configured with one or more components, names of which may vary with a type of the apparatus. The apparatus may include at least one of the foregoing elements, some of which may be omitted or to which other elements may be added. In addition, some of the elements of the apparatus according to various embodiments may be integrated into one entity to perform functions of the corresponding elements in the same manner as before they are integrated.

The examples and embodiments described herein serve to illustrate rather than limit the invention. The person skilled in the art will be able to design alternative embodiments without departing from the scope of the claims. Reference signs placed in parentheses in the claims shall not be interpreted to limit the scope of the claims. Items described as separate entities in the claims or the description may be implemented as a single hardware or software item combining the features of the items described.

The invention claimed is:

1. A method for magnetic resonance imaging (MRI) comprising:
   obtaining, from an MRI apparatus, an image acquisition sequence comprising RF pulses and magnetic field gradients configured to encode spatial information in a part of an object;
   obtaining a predetermined noise cancelling signal corresponding to the obtained image acquisition sequence at a first position;
   generating the image acquisition sequence, wherein the magnetic fields gradients are generated by gradient coils;
   converting, by an acoustic transducer, simultaneously with the generating the image acquisition sequence, the predetermined noise cancelling signal to an acoustic noise cancelling signal at the first position, wherein the predetermined noise cancelling signal is obtained based on an acoustic transfer function and the magnetic field gradients of the image acquisition sequence, wherein the acoustic transfer function is obtained by performing machine learning on one or more calibration image acquisition sequences obtained during a calibration state before the generating of the image acquisition sequence; and
   generating, by the acoustic transducer, the acoustic noise cancelling signal to cancel an acoustic noise of a gradient coil in the MRI apparatus.

2. An apparatus for magnetic resonance imaging of an object comprising:
   RF coils for generating RF pulses;
   gradient coils for generating gradient magnetic fields;
   an acoustic transducer; and
   a controller arranged to:
      obtain, from an MRI apparatus, an image acquisition sequence comprising the RF pulses and the gradient magnetic fields configured to encode spatial information in a part of the object;
      obtain a predetermined noise cancelling signal corresponding to the obtained image acquisition sequence at a first position inside the MRI apparatus;
      generate the image acquisition sequence;
      control the acoustic transducer to convert the predetermined noise cancelling signal to an acoustic noise cancelling signal at the first position, wherein the noise cancelling signal is obtained based on an acoustic transfer function and the magnetic field gradients of the image acquisition sequence, wherein the acoustic transfer function is obtained by performing machine learning on one or more calibration image acquisition sequences obtained during a calibration state before the generating of the image acquisition sequence; and
      generate, by the acoustic transducer, the acoustic noise cancelling signal to cancel an acoustic noise of a gradient coil in the MRI apparatus.

3. A method for magnetic resonance imaging (MRI) comprising:
   obtaining, from an MRI apparatus, an image acquisition sequence comprising RF pulses and magnetic field gradients configured to encode spatial information in a part of an object;
   obtaining a predetermined noise cancelling signal corresponding to the obtained image acquisition sequence at a first position;
   generating the image acquisition sequence, wherein the magnetic fields gradients are generated by gradient coils;
   converting, by an acoustic transducer, simultaneously with the generating the image acquisition sequence, the predetermined noise cancelling signal to an acoustic noise cancelling signal at the first position, wherein the noise cancelling signal is obtained based on an acoustic transfer function and the magnetic field gradients of the image acquisition sequence, wherein the predetermined noise cancelling signal is linearly related to Fourier transforms of time derivatives of a currents generated by the gradient coils during a calibration state before the generating of the image acquisition sequence; and
   generating, by the acoustic transducer, the acoustic noise cancelling signal to cancel an acoustic noise of a gradient coil in the MRI apparatus.

4. The method according to claim 1, wherein, in the calibration state, the method comprises
   generating calibration gradients through the gradient coils;
   acquiring, by a microphone at the first position, signals of an acoustic response caused by the generated calibration gradients.

5. The method according to claim 1, wherein performing machine learning comprises training a convolutional neural network (CNN) or a recurrent neural network (RNN).

6. The method according to claim 1, further comprising:
   generating combined magnetic field gradients for at least two orthogonal axes;
   acquiring, by a microphone at the first position, combined signals of the acoustic response of the combined magnetic field gradients;
   determining a predictive signal based on the transfer function and the combined magnetic gradients, and
   minimizing a difference between the acquired combined signal and the predictive signal by iterating the predictive signal over a range of values $t_{ph}$, wherein $t_{ph}$ is defined for combinations of at least two gradient pulses, wherein a phase correction for the transfer functions is based on $t_{ph}$ and applied to the acoustic transfer function.

7. The method according to claim 1, wherein performing machine learning comprises training a neural network.

8. The method according to claim 1, wherein performing machine learning comprises performing machine learning on one or more generic image acquisition sequences and the one or more calibration image acquisition sequences.

9. The apparatus according to claim 2, wherein the controller is further arranged to perform machine learning by training a convolutional neural network (CNN) or a recurrent neural network (RNN).

10. The apparatus according to claim 2, further comprising a microphone at the first position, and wherein the controller is further arranged to, in the calibration state:
    generate calibration gradients through the gradient coils; and
    acquire, via the microphone at the first position, signals of an acoustic response caused by the generated calibration gradients.

11. The apparatus according to claim 2, further comprising a microphone at the first position,
    wherein the gradient coils are further arranged to generate combined magnetic field gradients for at least two orthogonal axes; and
    wherein the controller is further arranged to:
    acquire, via the microphone at the first position, combined signals of the acoustic response of the combined magnetic field gradients;
    determine a predictive signal based on the transfer function and the combined magnetic gradients, and
    minimize a difference between the acquired combined signal and the predictive signal by iterating the predictive signal over a range of values $t_{ph}$, wherein $t_{ph}$ is defined for combinations of at least two gradient pulses, wherein a phase correction for the transfer functions is based on $t_{ph}$ and applied to the acoustic transfer function.

12. The apparatus according to claim 2, wherein the controller is further arranged to perform machine learning by performing machine learning on one or more generic image acquisition sequences and the one or more calibration image acquisition sequences.

13. The apparatus according to claim 2, wherein performing machine learning comprises training a neural network.

14. The method of claim 3, further comprising applying a phase shift and/or a latency correction to the predetermined noise signal during the calibration state.

15. The method according to claim 4, wherein performing machine learning comprises training a temporal recurrent neural network on the calibration magnetic field gradients of the one or more calibration image acquisition sequences and the signals of the acoustic response.

16. The method according to claim 4, further comprising:
    determining a latency correction by minimizing a difference between the acquired acoustic response and a predicted acoustic response by iterating over a range of candidate latency corrections.

17. The method according to claim 8, wherein the machine learning comprises first training a neural network on the one or more generic image acquisition sequences and subsequently training the neural network on the one or more calibration image acquisition sequences.

18. The method according to claim 8, wherein the machine learning comprises jointly training a neural network on the one or more generic image acquisition sequences and the one or more calibration image acquisition sequences.

19. The apparatus according to claim 10, wherein the controller is further arranged to:
   perform machine learning by training a temporal recurrent neural network based on the calibration magnetic field gradients of the calibration image acquisitions sequences and the signals of the acoustic response.

20. The apparatus according to claim 10, wherein the controller is further arranged to determine a latency correction by minimizing a difference between the acquired acoustic response and a predicted acoustic response by iterating over a range of candidate latency corrections.

* * * * *